(12) United States Patent
Kobayashi et al.

(10) Patent No.: US 7,781,607 B2
(45) Date of Patent: Aug. 24, 2010

(54) METHOD FOR PRODUCING POLYMERIZED COORDINATION COMPOUNDS OF PLATINUM COMPLEX

(75) Inventors: Katsutoshi Kobayashi, Kashiwa (JP); Shoko Nagasaki, Kashiwa (JP); Kazunori Kataoka, Tokyo (JP); Chieko Tsuchiya, Kashiwa (JP)

(73) Assignees: Nanocarrier Co., Ltd., Chiba (JP); The University of Tokyo, Tokyo (JP)

( * ) Notice: Subject to any disclaimer, the term of this patent is extended or adjusted under 35 U.S.C. 154(b) by 24 days.

(21) Appl. No.: 11/921,784

(22) PCT Filed: Jun. 8, 2006

(86) PCT No.: PCT/JP2006/311969

§ 371 (c)(1),
(2), (4) Date: Jan. 7, 2008

(87) PCT Pub. No.: WO2006/132430

PCT Pub. Date: Dec. 14, 2006

(65) Prior Publication Data

US 2008/0249256 A1    Oct. 9, 2008

(30) Foreign Application Priority Data

Jun. 9, 2005  (JP) .............................. 2005-169917

(51) Int. Cl.
*A61K 9/14*    (2006.01)
(52) U.S. Cl. ................. 556/486; 424/78.08; 424/78.17; 424/450; 424/489; 424/649; 514/184; 514/492; 514/772.3; 514/772.6; 525/434
(58) Field of Classification Search ................. 260/429, 260/366; 424/78.17, 78.08; 514/184, 492
See application file for complete search history.

(56) References Cited

U.S. PATENT DOCUMENTS

| | | | | |
|---|---|---|---|---|
| 4,115,418 A | * | 9/1978 | Gale et al. ................... | 556/137 |
| 4,200,583 A | * | 4/1980 | Kidani et al. ................. | 536/55 |
| 4,485,093 A | * | 11/1984 | Runge ..................... | 424/181.1 |
| 4,931,553 A | * | 6/1990 | Gill et al. .................. | 424/78.26 |
| 5,087,616 A | * | 2/1992 | Myers et al. .................. | 514/21 |
| 5,693,751 A | * | 12/1997 | Sakurai et al. .............. | 530/322 |
| 7,125,546 B2 | * | 10/2006 | Kataoka et al. .......... | 424/78.17 |

FOREIGN PATENT DOCUMENTS

| | | |
|---|---|---|
| JP | 03-095196 | 4/1991 |
| JP | 09-040685 | 2/1997 |
| JP | 09-132583 | 5/1997 |
| JP | 2003-342168 | 12/2003 |
| WO | PCT/FR97/00419 | * 3/1997 |
| WO | 02/26241 | 4/2002 |
| WO | 2004/082718 | 9/2004 |

OTHER PUBLICATIONS

Nishiyama, Nobuhiro, et al.; Langmuir, 1999, 15 (2), p. 377-383.*
Y. Ohya et al. "Synthesis and cytotoxic activity of dextran carrying cis-dichloro(cyclohexane-trans-I-1,2-diamine)platinum(II) complex", Biomater. Sci. Polymer Edn., vol. 7, No. 12, pp. 1085-1096 (1996).
Horacio Cabral et al., "Preparation and biological properties of dichloro(1,2-diaminocyclohexane)platinum(II)(DACHPt)-loaded polymeric micelles", Journal of Controlled Release, vol. 101, pp. 223-232 (2005).

* cited by examiner

*Primary Examiner*—David Wu
*Assistant Examiner*—Robert Jones, Jr.
(74) *Attorney, Agent, or Firm*—Wenderoth, Lind & Ponack, L.L.P.

(57) ABSTRACT

There is provided a production method in which bis(nitrato) platinum complex, optionally in the concurrent presence of dihalo-platinum complex, and poly(ethylene glycol)-block-poly(glutamic acid) are used at specific ratios and reacted. Coordination compound of an anti-tumor platinum complex with a block copolymer having carboxyl groups on its side chains is efficiently produced.

15 Claims, 7 Drawing Sheets

METHOD FOR PRODUCING POLYMERIZED COORDINATION COMPOUNDS OF PLATINUM COMPLEX

TECHNICAL FIELD

The present invention relates to a method for producing a conjugate, in particular, a coordination compound, of a platinum complex useful as an anti-tumor agent and a block copolymer.

BACKGROUND ART

A certain kind of platinum complexes are useful as anti-tumor agent, and some of them have already been put to clinical use. In particular, specific stereoisomers of dichloro (1,2-cyclohexanediamine)platinum(II) (hereinafter may be abbreviated as "Dach-Pt(chlorato)" in some cases) have been developed as analogs of cisplatin which has been clinically used of old as an anti-tumor agent, and great interest has been taken in them because of their anti-tumor activity superior to that of cisplatin. Dach-Pt(chlorato) did not come to be clinically used mainly because of its low water-solubility. Whereas, cis-[(1R2R)]-1,2-cyclohexanediamine-N,N']oxalate(2-)-O,O-platinum(II) (this is also called oxaliplatin), one of various compounds of modified Dach-Pt(chlorato) in which two chlorato groups, that are leaving ligands in the molecule, are substituted with oxalato groups, are currently widely used for clinical therapy due to its good water-solubility and potent anti-tumor activity.

With the view to impart still improved properties, conjugates of Dach-Pt with, for example, oxidized dextran or carboxymethoxydextran which are obtained by substituting the chlorato groups of Dach-Pt(chlorato) with a polymer having carboxyl groups on its side chains (see Non-patent document 1; cited documents are collectively listed later) and conjugate of poly(ethylene glycol)-block-poly(glutamic acid) and Dach-Pt (see Non-patent document 2) have been also provided. In particular, the Non-patent document 2 discloses that the conjugate described therein forms a polymer micelle and is solubilized in an aqueous medium, and shows not only anti-tumor activity comparable to oxaliplatin but also high drug stability and prolonged, high tumor accumulation.

In the Non-patent document 1, the substitution of the chlorato groups of Dach-Pt(chlorato) with the polymer is carried out by treating the Dach-Pt(chlorato) with silver nitrate, removing the resulting silver chloride by filtration, converting the filtrate to corresponding diaquo-complex (occasionally abbreviated as Dach-Pt(hydroxo)) having improved water-solubility, by passing through anion-exchange resin, and reacting the complex with the polymer in water (see page 1088 of the document). In the Non-patent document 2, almost the same procedure is also carried out except that the silver chloride produced is removed by centrifugation (see the right column at page 226 of the document).

LIST OF CITED DOCUMENTS

Non-patent document 1: Y. OHYA et al., J. Biomater. Sci. Polymer Edn., Vol. 7, pp. 1085-1096 (1996)
Non-patent document 2: H. Cabral et al., J. Controlled Release, 101 (2005) 223-232

DISCLOSURE OF THE INVENTION

The conjugate of poly(ethylene glycol)-block-poly(glutamaic acid) and Dach-Pt which was prepared according to the method described in the Non-patent document 2 formed polymer micelles in an aqueous medium, which specifically were polymer micelles prepared from [DACHPt]/[Glu]=0.75, and their cumulant-diameter was 40 nm and cumulant-polydispersity was considerably low ($\mu_2/\Gamma^2$=0.03) in accordance with the measurement of their dynamic light scattering (DLS). When the present inventors reproduced this method, presence of silver ion was detected as mixed in the Dach-Pt conjugate, and it was impossible or extremely difficult to remove such silver ion from the produced conjugate by conventional methods. This is probably because the silver ion, which was not removed by the centrifugation, was taken into the polymer micelles. For medical preparations to be administered to living body, mixed presence of such silver ion must be avoided as much as possible.

Thus, an objective of the present invention is to provide a substantially silver ion-free conjugate (or a coordination compound) of a block copolymer with a platinum complex, especially a conjugate of a block copolymer with Dach-Pt. One method to achieve the objective is to thoroughly remove silver ion before a conjugate of a block copolymer and platinum complex is formed. As described in the Non-patent document 1, diaquo-platinum complex from which silver ion has been thoroughly removed may be used. Whereas, the present inventors found that the objective of the present invention could also be accomplished when the thorough silver ion elimination was carried out at the stage of bis (nitrato)-platinum complex which corresponds to a precursor of the diaquo-platinum complex and the resulting product was used as the starting material of the platinum complex.

Furthermore, we also found that a solution containing polymer micelles showing single peak could be provided by reducing or eliminating those peaks which were attributable to polydispersed or aggregated micelles, when the polymer micelles produced in an aqueous medium from the polymer/platinum complex conjugate was analyzed by gel permeation chromatography (GPC), once the use ratio of bis(nitrato) platinum complex and the block copolymer was set at a specific numerical value.

Surprisingly, we further found that use of a mixture of diaquo-platinum complex or bis(nitrato)platinum complex with dihalo-platinum complex (dichloro-, diiodo-, or dibromo-platinum complex) as the starting material of the platinum complex could provide a solution containing polymer micelles having similar single peak and still narrower particle size distribution.

Thus, according to the present invention, there is provided a method for producing a coordination compound through reaction of platinum complex with a polymer having carboxyl groups on its side chains, wherein a mixture of diaquo-platinum complex or bis(nitrato)platinum complex, in particular, the latter, with dihalo-platinum complex (dichloro-, diiodo, or dibromo-platinum complex) is used as the platinum complex; and a block copolymer represented by the following general formula (1) or (2):

-continued (2)

wherein $R^1$ represents hydrogen atom or an unsubstituted or substituted linear or branched $C_1$-$C_{12}$ alkyl group; $L^1$ and $L^2$ each independently represents a linking group; $R^2$ represents methylene group or ethylene group; $R^3$ represents hydrogen atom, a protecting group of amino group, hydrophobic group or a polymerizable group; $R^4$ represents hydroxyl group, protected carboxyl group as formed together with the terminal —CO, or a hydrophobic group; $R^5$s each independently represents a hydrogen atom, an alkali metal ion or a protecting group of carboxyl group; m represents an integer of 5 to 20,000, n represents an integer of 2 to 5,000, and x represents an integer of 0 to 5,000, with the proviso that x is not larger than n, and hydrogen atom or alkali metal ion occupies 50% or more, preferably 80% or more, and more preferably 100%, of n–x and x $R^5$s, is used as the polymer, the method comprising a step of carrying out the reaction in an aqueous medium under the condition that the platinum complex (including platinum complexes in mixed state) and the block copolymer mutually form a coordination compound, and a step of recovering the so formed coordination compound.

In a preferred embodiment according to the present invention, diaquo(1,2-cyclohexanediamine)platinum(II) is used as the diaquo-platinum complex, bis(nitrato)(1,2-cyclohexanediamine)platinum(II) is used as the bis(nitrato)platinum complex, and dichloro(1,2-cyclohexanediamine)platinum (II) is used as the dihalo-platinum complex.

According to another embodiment of the present invention, there is also provided a method for producing coordination compound through reaction of a platinum complex with a polymer having carboxyl groups on its side chains, wherein as the starting material bis(nitrato)(1,2-cyclohexanediamine)platinum(II), diaquo(1,2-cyclohexanediamine)platinum(II) or a mixture of bis(nitrato)(1,2-cyclohexanediamine)platinum(II) and diaquo(1,2-cyclohexanediamine)platinum(II) is used, the platinum complexes being substantially free of silver ion, and a block copolymer represented by the general formula (1) or (2) above is used as the polymer, the method comprising a step of carrying out the reaction in an aqueous medium under the conditions that the platinum complex (including the mixture of platinum complexes) and the block copolymer mutually form a coordination compound and a step of recovering thus obtained coordination compound. In a preferred embodiment of the present invention, the ratio of platinum atoms in all of the platinum complex(es), preferably bis(nitrato)(1,2-cyclohexanediamine)platinum(II) (hereinafter may be abbreviated as Dach-Pt(nitrate)), to carboxylate groups in the block copolymer (on equivalent basis, which applies hereafter) is set to be more than 0.4, preferably 0.45 or more to 0.7 or less, more preferably 0.475 or more to 0.6 or less, and most preferably 0.5 or more to 0.55 or less. Final concentration of total platinum complex(es) in the reaction liquid of the aqueous medium is set to be 2 mg/mL (approximately 4.6 mM) or less, preferably 1 mg/mL (approximately 2.3 mM) or less. Although these two setting conditions can be independently selected, simultaneous selection of both conditions leads to more preferable result.

When use of the conjugate of a block copolymer and a platinum complex, which is obtained according to the present invention, as anti-tumor agent is made the premise, particle size distribution of the polymer micelles is an important factor for accumulating the drug in tumor through the enhanced permeability and retention (EPR) effect. According to the present invention, there is provided a solution containing polymer micelles which show a single peak on GPC measurement and furthermore a peak of narrow distribution of cumulant diameter which is one of the criteria for particle diameter, namely a narrow particle size distribution. Therefore, according to the present invention, there is provided an effective method for producing conjugates or coordination compounds that can be conveniently used as anti-tumor agents, for example those which can form polymer micelles suitable for providing stable and excellent EPR effect.

Detailed description of the present invention is given below.

Main terms as used in the present specification, which are considered to require standard definitions, should be understood as follows, although not to be limited thereby.

A coordination compound is a compound which is considered to contain coordination bond(s), wherein the coordinate bond exists between platinum of a platinum complex and a carboxyl group of a block copolymer. In the specification, the term "conjugate" of the block copolymer and platinum complex is used in the sense interchangeable with coordination compound.

Diaquoplatinum complex, bis(nitrato)-platinum complex or dihaloplatinum complex (dichloro-, diiodo-, or dibromoplatinum complex) which are useful platinum complexes, may contain any other ligand(s) besides diaquo, bis(nitrato) or dihalo ligands so long as they meet with the objective of the present invention. Examples include the following, but not limited to these. A diaquoplatinum complex may include diaquo(1,2-cyclohexanediamine)platinum(II), cis-diamine-diaquoplatinum (II), amino-diaquo-cyclohexylamine platinum (II), cis-amine-diaquo(2-methylpyridine)platinum (II) and the like, and diaquo(1,2-cyclohexanediamine)platinum (II) is particularly preferred. A bis(nitrato)platinum complex may include bis(nitrato)(1,2-cyclohexanediamine)platinum (II), cis-diamine-dinitro platinum(II), amino-dinitro-cyclohexylamine platinum (II), cis-amine-dinitro(2-methylpyridine)-platinum(II) and the like, and bis(nitrato)(1,2-cyclohexanediamine)platinum(II) is particularly preferred. Among dihalo-platinum complexes (dichloro-, diiodo- or dibromoplatinum complex), dichloroplatinum complex can be preferably used, it may include dichloro(1,2-cyclohexanediamine)platinum complex, cis-diamine-dichloro-platinum(II), amino-dichloro-cyclohexylamine platinum(II), and cis-amine dichloro(2-methylpyridine)platinum(II) and the like, and dichloro(1,2-cyclohexanediamine)platinum(II) is particularly preferred.

"Substantially silver ion-free" means a condition that at the maximum not more than 20 ppm of silver is contained, and preferably silver cannot be detected by conventional methods (for example, atomic absorption method) or not contained at all. Substantially silver ion-free diaquoplatinum complex or bis(nitrato)platinum complex, which are used as the starting material for the platinum complex, can be obtained by treating the corresponding dichloroplatinum complex with silver nitrate, removing the produced silver chloride precipitate, and further removing the still remaining silver ion with, for example, reverse osmosis membrane, as described in JP Hei 5(1993)-301884A. Useful method for their preparation, however, is not limited thereto. Furthermore, bis(nitrato)platinum complexes of this grade, for example, Dach-Pt(nitrato), is commercially available from W.C. Heraeus GmbH & Co. KG. Such Dach-Pt(nitrato) is bis(nitrato)(1,2-cyclohexanediamine)platinum(II) (it is also referred to as diaquo(1,2-cyclohexanediamine)platinum(II) dinitrate). While these platinum complexes may be any existent stereoisomers, cis-dichloro (trans-L-1,2-cyclohexanediamine) and other platinum complexes having equivalent steric configuration are preferred.

In the present invention, any block copolymer represented by the above general formula (1) or (2) can be used to achieve the objective of the present invention. Whereas, preferred block copolymers are those represented by the following general formula (1-a) or (2-a) or their salts:

wherein $R^1$, $L^1$, $L^2$, $R^3$, $R^4$ and $R^5$ are the same as defined as to the general formulae (1) and (2), respectively; m represents an integer of 5 to 20,000; and n represents an integer of 10 to 60, provided that among n $R^5$s, hydrogen atom or alkali metal ion occupies 50% or more, preferably 80% or more, more preferably 100%.

Above definitions of the groups or moieties in the general formulae (1), (2), (1-a) and (2-a) should be interpreted in line with their meanings or contents as generally accepted by those skilled in the art. Specific examples thereof are given hereafter, but not limited thereto.

For $R^1$, an unsubstituted or substituted, linear or branched $C_1$-$C_{12}$ alkyl group includes methyl, ethyl, n-propyl, iso-propyl, n-butyl, sec-butyl, tert-butyl, n-pentyl, n-hexyl, decyl and undecyl. In case of substituted $R^1$, substituent includes an acetalized formyl group, cyano group, formyl group, carboxyl group, amino group, $C_1$-$C_6$ alkoxycarbonyl group, $C_2$-$C_7$ acylamido group, the same or different tri-$C_1$-$C_6$ alkylsiloxy group, siloxy group, or silylamino group. Poly(ethylene glycol) (PEG) segments having such a functional group at their one of the terminals can be conveniently produced according to those manufacturing methods for PEG segments of block polymers as described in, for example, WO96/32434, WO96/33233 and WO97/06202.

The block copolymers represented by the general formulae (1), (2), (1-a) or (2-a) thus produced can take any mode of linking depending on the manufacturing method used, and may be linked by any linking group so long as they meet the objective of the invention. For example, the methods include a method for producing object block copolymer by using a PEG derivative having a terminal amino group, polymerizing the same utilizing its amino terminal with, for example, N-carboxylic acid anhydride (NCA) of β-benzyl-L-aspartate and/or γ-benzyl-L-glutamate, to synthesize a block copolymer, and then either converting the side chain benzyl groups to other ester groups or partially or completely hydrolyzing them. In this case, the structure of the copolymer becomes one represented by the general formula (1) or (1-a), and the linking group $L^1$ has a structure derived from the terminal structure of the PEG segment used, which preferably is —$(CH_2)_b$—NH— (in which b is an integer of 1 to 5).

Furthermore, the copolymer according to the present invention can be produced by a method in which poly(carboxylic acid) or poly(amino acid or a derivative thereof) segment moiety is synthesized and then it is bound to a preliminarily prepared PEG segment moiety. In this case, the copolymer produced may eventually have the same structure with that of the copolymer produced by the first described method, or a structure corresponding to the general formula (2) or (2-a). While the linking group $L^2$ is not particularly limited, preferably it is —$(CH_2)_c$—CO— (in which c is an integer of 1 to 5).

$R^5$ can be each independently hydrogen atom or a protecting group of carboxyl group. The protecting group of carboxyl group includes, but not limited thereto, benzyl, benzhydryl or $C_{1-6}$ alkyl group, specific examples of alkyl group being methyl, ethyl, n-propyl, iso-propyl, n-butyl, sec-butyl, t-butyl, n-pentyl and n-hexyl.

$R^3$ can be each independently hydrogen atom or a protecting group of amino group, for example, benzyloxycarbonyl, t-butyloxycarbonyl, acetyl or trifluoroacetyl group, and it can also be a hydrophobic group such as benzylcarbonyl or benzhydrylcarbonyl group and the like, or a polymerizable group such as acryloyl or methacryloyl group.

$R^4$ can be each independently hydroxyl group; protected carboxyl group with the terminal —CO, for example, benzyloxy carbonyl, t-butyloxycarbonyl or methoxycarbonyl group; a hydrophobic group such as benzyloxy or benzhydryloxy group; or a polymerizable hydrophobic group such as allyloxy or vinylphenylmethoxy group. m is an integer of 5 to 20,000, preferably 10 to 5,000, more preferably 40 to 500, and n is an integer of 2 to 5,000, preferably 5 to 1,000, more preferably 10 to 60, and most preferably 15 to 40. Therefore, although the moiety is expediently referred to as poly(ethylene glycol) or the like in the present specification, the prefix, "poly", is used as a concept inclusive of also those which normally fall under the category of "oligo".

Whereas, x, which determines the constitution ratio of two kinds of repeating units which can be present in the poly (amino acid or derivative thereof) segment, particularly poly (aspartic acid), can be an integer of 0 to 5,000 (but not larger than n). In this case, each of the repeating units can be distributed randomly or in blocks.

The reaction conditions for forming the above described coordination compound comprising platinum complex and block copolymer include diaquoplatinum complex, in particular, Dach-Pt(hydroxo) or bis(nitrato)platinum complex, in particular, Dach-Pt(nitrato), to be present in an aqueous medium, in particular, water (which can be an aqueous solution containing a water-miscible organic solvent such as methanol, ethanol, acetonitrile, dimethylformamide or the like, where necessary), in an amount soluble in the aqueous medium at temperatures ranging 5° C.-90° C., although not limited thereto; then concurrent presence of the block copolymer; and gently stirring the mixture or allowing the mixture to stand, for a time sufficient for formation of the coordination compound. Although it is impossible to specify the sufficient time because it varies depending on the reaction temperature, it can be 10 to 96 hours at 37° C.

When diaquoplatinum complex, especially Dach-Pt(hydroxo), or bis(nitrato)platinum complex, especially Dach-Pt(nitrato), is solely used as a starting material of platinum complex, the use ratio of platinum atoms in the platinum complex to carboxylate groups in the block copolymer (equivalent basis, the same shall apply hereinafter) desirably is set to be more than 0.4, preferably 0.45 or more to 0.7 or less, more preferably 0.475 or more to 0.6 or less, most preferably 0.5 or more to 0.55 or less. Coordination compounds obtained under such conditions form few or no aggregated polymer micelle in an aqueous medium and can form polymer micelles having virtually single peak as measured by GPC. Furthermore, the micelles can encapsulate about 80% or more of the platinum complex which is used in the reaction (charged amount).

Another preferred embodiment of the present invention is a method in which, as the starting materials of the platinum complex, a diaquoplatinum complex or a bis(nitrato)platinum complex, preferably Dach-Pt(hydroxo) or Dach-Pt(nitrato), especially Dach-Pt(nitrato), and a dihaloplatinum complex, preferably Dach-Pt(halogeno), especially dichloroplatinum complex, preferably Dach-Pt(chlorato) are caused to be present in an aqueous medium in mixed state and reacted with a block copolymer.

While the scope of the present invention is not to be theoretically limited, it can be assumed that in the coexistence of dihaloplatinum complex in this method allows to maintain the initial concentration of bis(nitrato)platinum complex, which reacts with the block copolymer in the reaction solution, at a low level so that the coordination compound is produced at an appropriate reaction rate to form the polymer micelles. Therefore, it is possible to form polymer micelles having virtually single peak as measured by GPC, with little or no formation of aggregated polymer micelle, under the broad range of use ratio between the platinum complex and the polymer, to provide a liquid reaction mixture which contains the polymer micelles having a narrow particle size distribution.

In Example 10 of Japanese Patent Publication No. 2000-506855A (or WO97/33894), there is a disclosure stating that boiling of equimolar amounts of Dach-Pt(chlorato) and Dach-Pt(nitrato) in distilled water results in production of binuclear platinum complex (that is, a platinum complex having two platinum atoms in one molecule).

Thus, although it gives rise to an assumption that the coordination compound according to the present invention may also be produced via the binuclear complex in the presence of the block copolymer according to the present invention, it is understood that the coordination compound produced in the present invention and forms the polymer micelles mainly carries a mono-nuclear platinum complex, when the factors including the nature of the reaction mixture are considered.

In the present invention, bis(nitrato)platinum complex, preferably Dach-Pt(nitrato) and dihaloplatinum complex, especially dichloroplatinum complex, preferably Dach-Pt(halogeno), especially Dach-Pt(chlorato) can be mixed or concurrently present in the aqueous medium at a molar ratio of 1:9 to 9:1, preferably 1:4 to 4:1, and more preferably 1:1. Such mixed or coexisting condition is preferably brought about by mixing bis(nitrato)platinum complex and dihaloplatinum complex in an aqueous medium, especially in water. Whereas, it is also possible to bring about the mixed or coexisting condition by causing Dach-Pt(halogeno), especially dichloroplatinum complex, preferably Dach-Pt(chlorato), to coexist with a strong acid except hydrochloric acid, such as sulfuric acid, perchloric acid, trifluoromethanesulfonic acid, nitric acid, especially nitric acid; or having an aqueous solution of bis(nitrato)platinum complex contain halide ion selected from the group consisting of chloride, iodide and bromide ions, to produce a prescribed amount of dihaloplatinum complex in situ. Source of such halide includes, although not limited thereto, hydrochloric acid, sodium chloride and potassium chloride for chloride ion; sodium iodide and potassium iodide for iodide ion; and potassium bromide, sodium bromide and hydrobromic acid for bromide ion. When such two platinum complexes coexist, the use ratio of the platinum complexes to block copolymer can be 4:10 to 4:1, preferably 4.5:10 to 2:1, more preferably 5:10 to 3:2, in terms of the ratio (equivalent ratio) of platinum atoms in the platinum complexes to carboxylate groups in the block copolymer.

Desired coordination compound is thus produced. The coordination compound can be efficiently recovered or purified by using conventional methods for separating a polymer micelle, for example, dialysis or ultrafiltration or combination thereof because the compound automatically associates and forms stable polymer micelles encapsulating the platinum complexes in the reaction solution.

BEST MODE FOR CARRYING OUT THE INVENTION

Hereinafter the present invention is described more specifically, referring to specific examples which however are not intended to limit the present invention. Further, in the following examples, platinum complexes of which silver ion content was less than 5 ppm were used.

Example 1

This Example describes a specific example in which Dach-Pt(nitrato) and Dach-Pt(chlorato) coexist as stating materials.

Figure 1:
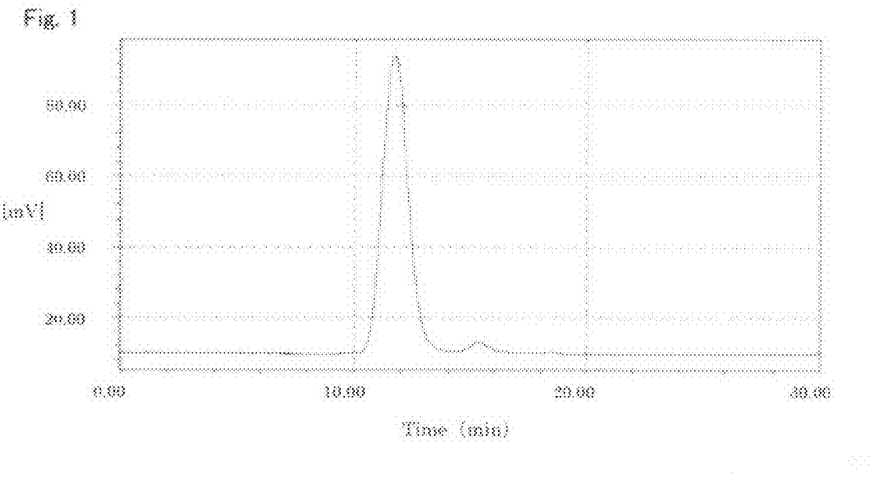
FIG. 1 is a GPC chart of the polymer micelle-containing solution as obtained in Example 1. The abscissa axis represents the retention time (minutes) and the ordinate axis represents the output (mV) of ultraviolet absorptiometer.
Figure 2:
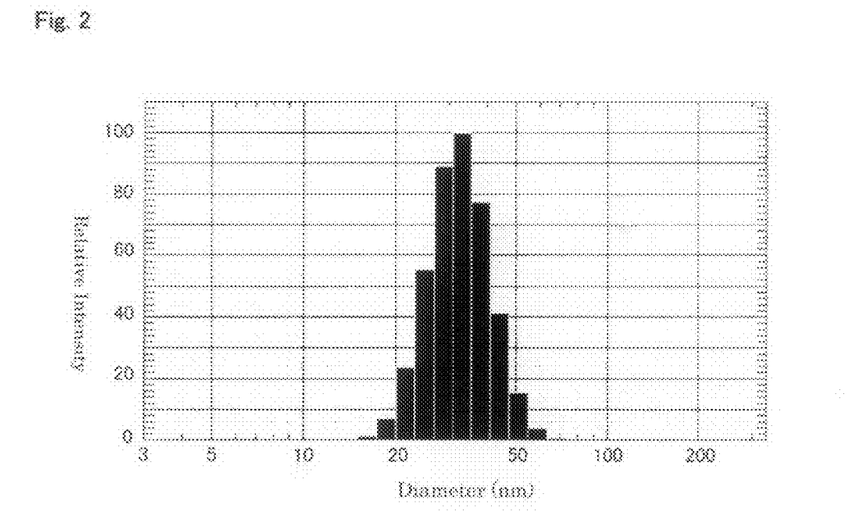
FIG. 2 is a graph showing particle size distribution of the micelles in the polymer micelle-containing solution as obtained in Example 1, which was measured by dynamic light scattering method. The abscissa axis represents the diameter (nm) and the ordinate axis represents relative intensity.

To 217 mg of bis(nitrato)(trans-L-1,2-diaminocyclohexane)platinum(II) [which is also referred to as cis-diaquo (trans-L-1,2-cyclohexanediamine)platinum(II) nitrate and hereinafter this nomenclature is used] and 189 mg of dichloro (trans-L-1,2-diaminocyclohexane)platinum(II) [or cis-dichloro(trans-L-1,2-cyclohexanediamine)platinum(II), and hereinafter this nomenclature is used], 220 mL of water was added and together heated up to 70° C. to dissolve the two. This solution was cooled to about 37° C., and 750 mg of poly(ethylene glycol)-block-poly(glutamic acid) [hereinafter abbreviated as PEG-P(Glu)), and when molecular weight of PEG is 12×10³ and polymerization degree of P(Glu) is 20, the copolymer is abbreviated as PEG-P(Glu)12-20] was dissolved therein {[cis-diaquo(trans-L-1,2-cyclohexanediamine)platinum(II) nitrate+cis-dichloro(trans-L-1,2-cyclohexanediamine)platinum(II)]/[Glu]=1}, and it was allowed to react at 37° C. for 72 hours in a dark place. The solution obtained was subjected repeatedly to ultrafiltration through an ultrafiltration apparatus (Nippon Millipore: Labscale•TFF system: molecular weight cutoff 100,000) to remove most of the low molecular byproducts, $NaNO_3$ and NaCl, and unreacted platinum complex and block copolymer which did not form micelles. The filtrate was concentrated to provide 55 mL of the micelle solution. The amount of the platinum complex encapsulated in the micelles was 38% of the added amount. GPC analysis of the solution by liquid chromatography (TOSOH Corporation, AS-8020 series) was performed under the following GPC conditions. The GPC chart is shown in FIG. 1. Separately, dynamic light scattering measurement (NICOMP.380ZLS) was carried out according to the attached manual. The result is shown in FIG. 2.

GPC conditions
Column: Waters Ultrahydrogel 500
10 µm 7.8×300 mm
Detector: Ultraviolet absorptiometer (measuring wavelength=240 nm)
Column temperature: about 40° C.
Mobile phase: 10 mmol/L phosphate buffer (pH 7.4)
Flow rate: 0.6 mL/min
Sample Injection volume: 10 µL As is apparent from FIG. 1, it is understood that aggregated polymer micelles or those having very large diameter were not formed because no peak was observed on the high molecular weight side (shorter retention time). From FIG. 2, it is also understood that the average particle diameter of the formed polymer micelles was 33.3 nm with the standard deviation of 7.9 nm (23.7%).

Example 2

This Example describes a specific example in which Dach-Pt(nitrato) alone was used as the starting material and a coordination compound was formed at a specific ratio relative to carboxylate(Glu) in a block copolymer.

Figure 3:
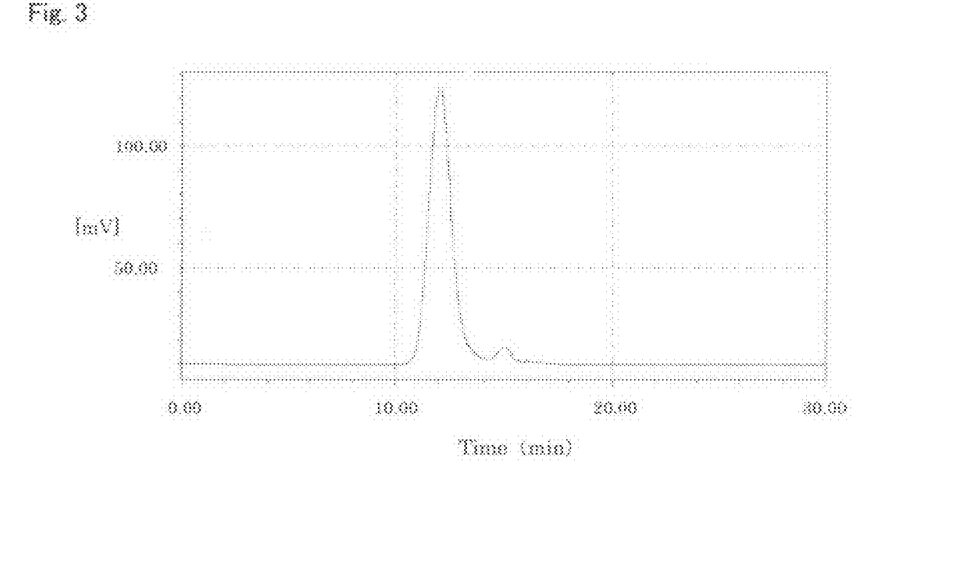
FIG. 3 is a GPC chart of the polymer micelle-containing solution as obtained in Example 2. The abscissa axis and the ordinate axis have the same meanings as in FIG. 1.
Figure 4:
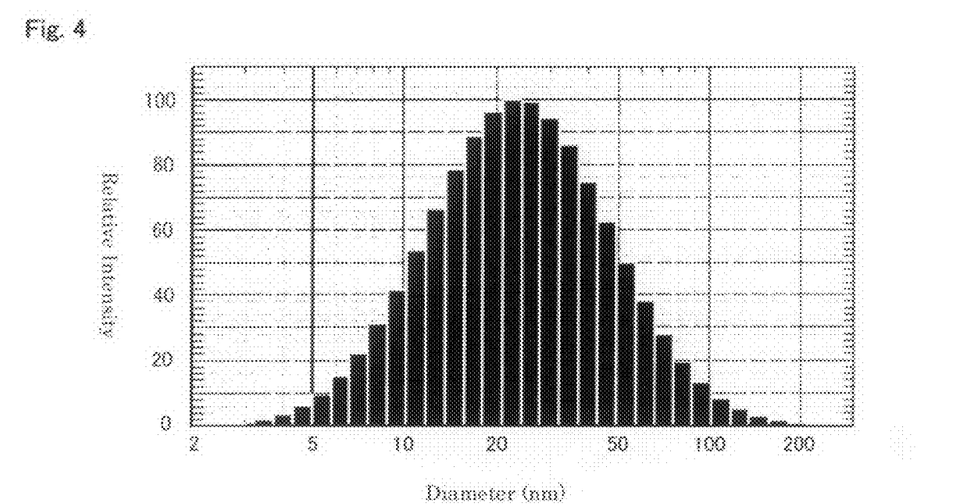
FIG. 4 is a graph showing particle size distribution of the micelles in the polymer micelle-containing solution as obtained in Example 2, which was measured by dynamic light scattering method. The abscissa axis and the ordinate axis have the same meanings as in FIG. 2.

To 227 mg of cis-diaquo(trans-L-1,2-cyclohexanediamine)platinum(II) nitrate, 120 mL of water was added and heated to 70° C. to form a solution. This solution was cooled to about 37° C., and 750 mg of PEG-P(Glu) 12-20 was dissolved therein {[cis-diaquo(trans-L-1,2-cyclohexanediamine)platinum (II) nitrate]/[Glu]=0.525} and the solution was allowed to react at 37° C. for 72 hours in a dark place. Thus obtained solution was repeatedly subjected to ultrafiltration (molecular weight cutoff 100,000) to remove most of the low molecular byproduct, $NaNO_3$, and unreacted platinum complex and block copolymer which did not form micelles. This solution was subjected to GPC analysis as in Example 1. The GPC chart is shown in FIG. 3. The result of separately conducted dynamic light scattering measurement (NICOMP 380ZLS) is shown in FIG. 4.

From FIG. 3, it is understood that aggregated polymer micelles or those having very large diameter were not formed, because no peak was observed on the high molecular weight side. From FIG. 4, it is also understood that the average particle diameter of the formed polymer micelles was 29.9 nm with the standard deviation of 20.7 nm (69.0%). Although the polymer micelles had a wider size distribution as compared with those obtained in Example 1, no aggregated polymer micelle was observed.

Example 3

This example used Dach-Pt(nitrato) alone as the starting material and investigated the effect of the use ratio of platinum atoms in the platinum complex to the carboxylate (Glu) in the block copolymer on the configuration of the polymer micelles formed from the coordination compound.

Figure 5:
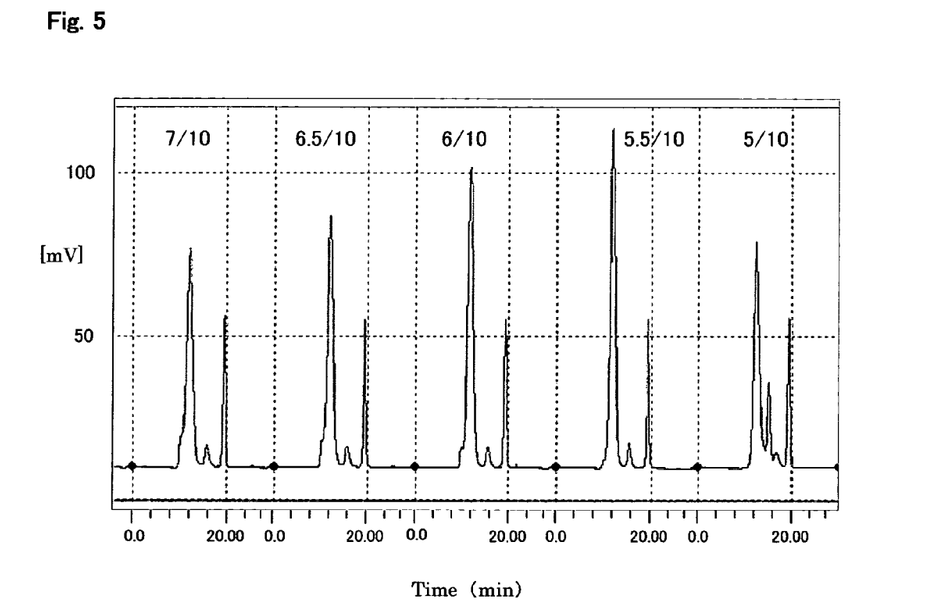
FIG. 5 shows GPC charts of each of the reaction solutions prepared by using platinum atoms in the platinum complex and carboxylate groups in the block copolymer at the ratios as given in Example 3. The abscissa axis and the ordinate axis have the same meanings as in FIG. 1.
Figure 6:
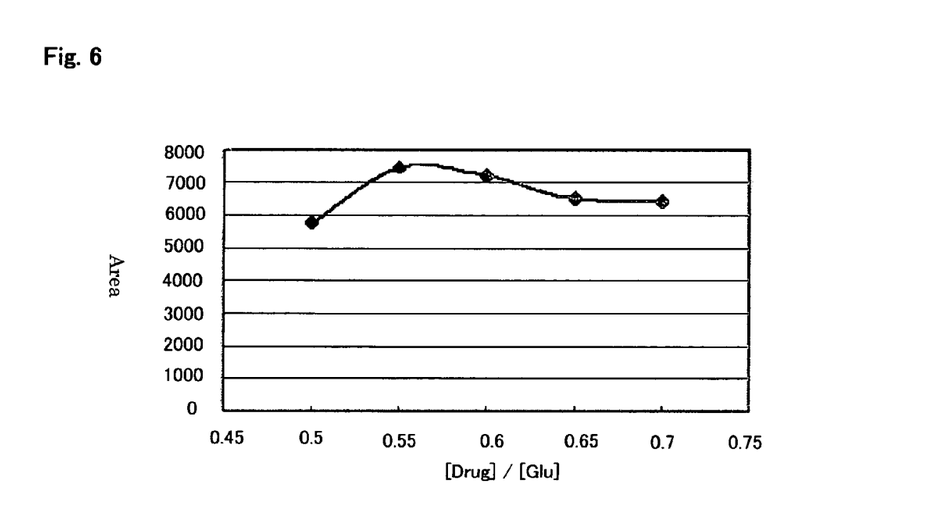
FIG. 6 is a graph showing the variation in the areas indicated in the GPC charts in FIG. 5, the areas corresponding to the amounts of respectively formed polymer micelles. The abscissa axis represents the use ratio of platinum atoms in the platinum complex to carboxylate groups in the block copolymer, and the ordinate axis represents the peak area [mV·sec.] of the micelles.

Cis-diaquo(trans-L-1,2-cyclohexanediamine)platinum(II) nitrate was dissolved in water at 70° C. (9.238 mmol/L). This solution was cooled to about 37° C., then aqueous PEG-P (Glu) 12-40 solution was added {[cis-diaquo(trans-L-1,2-cyclohexanediamine)platinum(II) nitrate]/[Glu]=7/10, 6.5/10, 6/10, 5.5/10 and 5/10}. The final concentration of cis-diaquo(trans-L-1,2-cyclohexanediamine)platinum(II) in each of the solutions was made 2 mg/mL (4.620 mmol/mL) and the solutions were allowed to react at 37° C. for 96 hours in a dark place. A portion of each of the resulting solutions was taken and subjected to GPC analysis under the same conditions as in Example 1. Thus obtained GPC charts are shown in FIG. 5. The correlation of the micellear area with [cis-diaquo(trans-L-1,2-cyclohexanediamine)platinum(II) nitrate]/[Glu] was as shown in FIG. 6. The micellar area reached the maximum when [cis-diaquo(trans-L-1,2-cyclohexanediamine)platinum(II) nitrate]/[Glu] was 5.5/10. From FIG. 5, it is inferred that those deemed to be aggregated polymer micelles were formed when the ratio of the platinum complex to the carboxylate was 7/10 to 6/10 because shoulder peaks were observed on the high molecular weight side.

Example 4

This example investigates the effect of the mixing ratio of two kinds of platinum complexes on the configuration of the polymer micelles formed from the coordination compounds.

Figure 7:
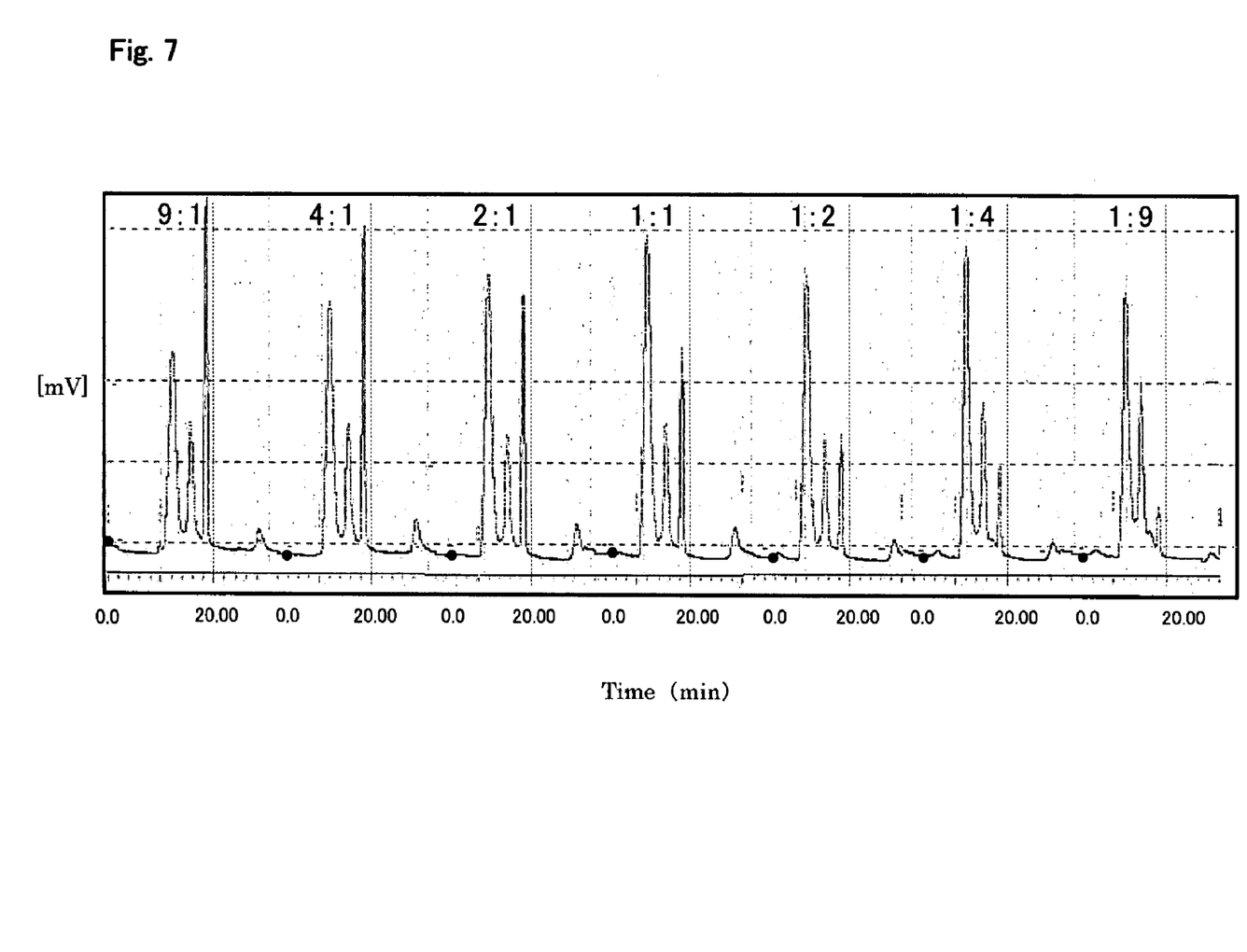
FIG. 7 shows GPC charts of the reaction solutions prepared by using two kinds of platinum complexes at the use ratios as given in Example 4. The abscissa axis and the ordinate axis have the same meanings as in FIG. 1.
Figure 8:
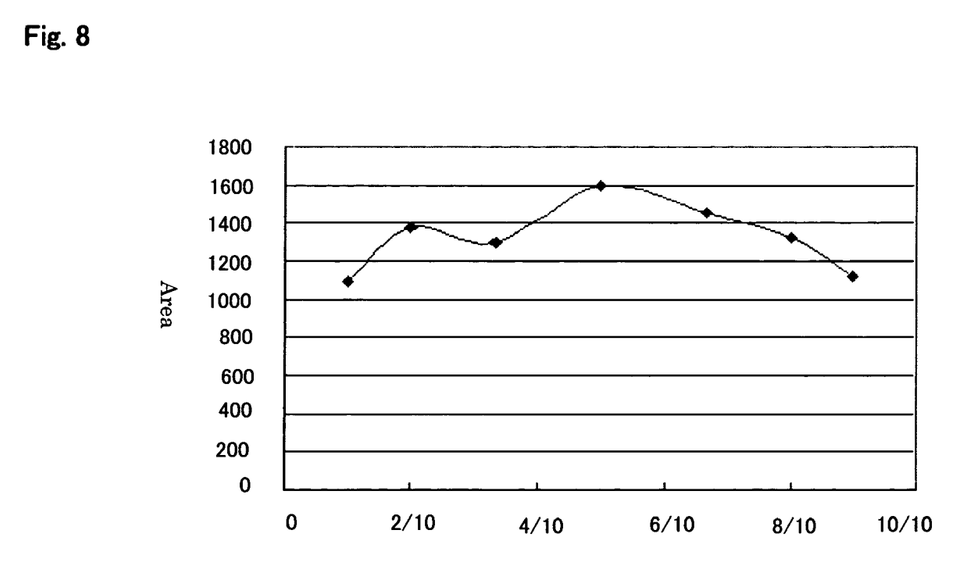
FIG. 8 is a graph showing the variation in the areas indicated in the GPC charts in FIG. 7, the areas corresponding to the amounts of respectively formed polymer micelles. The abscissa axis represents {[cis-diaquo(trans-L-1,2-cyclohexanediamine)platinum(II) nitrate]/([cis-dichloro(trans-L-1,2-cyclohexanediamine)platinum(II)]+[cis-diaquo(trans-L-1,2-cyclohexanediamine)platinum(II)]}, and the ordinate axis represents micelle's peak area [mV·sec].

Cis-diaquo (trans-L-1,2-cyclohexanediamine)platinum(II) nitrate and cis-dichloro(trans-L-1,2-cyclohexanediamine)platinum(II) were dissolved in water at 70° C. at the molar ratios 9:1, 4:1, 2:1, 1:1, 1:2, 1:4 and 1:9, respectively (total 2.5 mmol/L). Those solutions were cooled to about 37° C., in which PEG-P(Glu) 12-20 was dissolved {[cis-diaquo(trans-L-1,2-cyclohexanediamine)-platinum(II) nitrate+cis-dichloro(trans-L-1,2-cyclohexanediamine)platinum(II)]/[Glu]=1}, and the solutions were allowed to react at 37° C. for 72 hours in a dark place. A portion was taken from each of the reaction solutions and subjected to GPC analysis under the same conditions as in Example 1. Thus obtained GPC charts are shown in FIG. 7. The correlation of the micellar area with cis-diaquo(trans-L-1,2-cyclohexanediamine)platinum(II) nitrate:cis-dichloro(trans-L-1,2-cyclohexanediamine)platinum(II) was as shown in FIG. 8. The micellar area reached the maximum when cis-diaquo(trans-L-1,2-cyclohexanediamine)platinum(II) nitrate:cis-dichloro(trans-L-1,2-cyclohexanediamine)platinum(II) was 1:1.

Example 5

This example investigates the effect of the use ratio of platinum atoms in the platinum complexes to the carboxylate (Glu) in the block copolymer on the configuration of the polymer micelles formed of the coordination compounds, when two kinds of platinum complexes are used.

Figure 9:
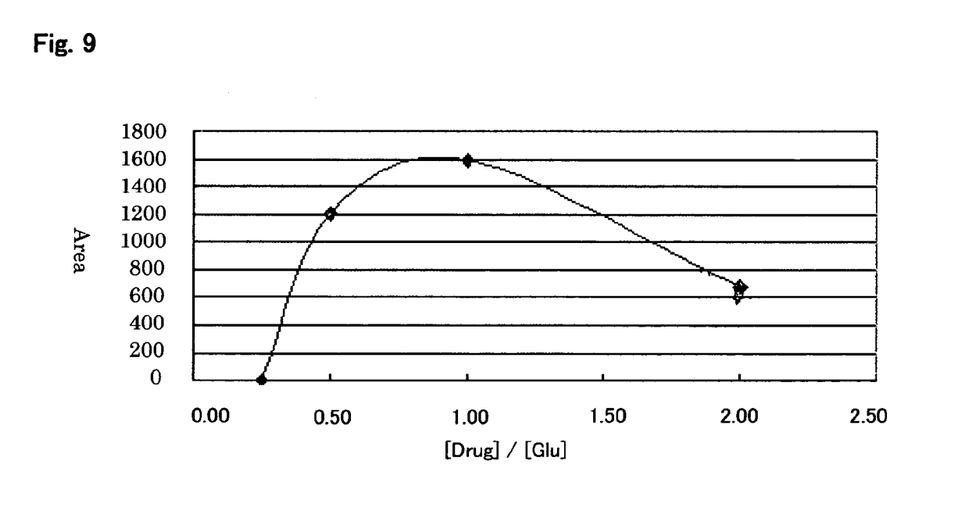
FIG. 9 is a graph showing the variation in the area corresponding to the amount of polymer micelles in each of the reaction solutions obtained at varied use ratio of platinum atoms in the equimolar mixture of two kinds of platinum complexes to carboxylate in the block copolymer in Example 5. The abscissa axis represents the use ratio of platinum atoms in the platinum complexes to carboxylate in the block copolymer, and the ordinate axis has the same meaning as in FIG. 8.

Cis-diaquo(trans-L-1,2-cyclohexanediamine)platinum(II) nitrate and cis-dichloro(trans-L-1,2-cyclohexanediamine) platinum(II) were dissolved in water at 70° C. at a molar ratio of 1:1 (total 2.5 mmol/L). This solution was cooled to about 37° C., and in which PEG P(Glu) 12-20 was dissolved at the [cis-diaquo(trans-L-1,2-cyclohexanediamine)platinum(II) nitrate+cis-dichloro(trans-L-1,2-cyclohexanediamine)platinum(II)]/[Glu] ratios of 1/4, 1/2, 1/1 or 1/0.5. Then resulting solutions were allowed to react at 37° C. for 24 hours in a dark place. A portion of each of the reaction solutions was taken and subjected to GPC analysis under the same conditions as in Example 1. The correlation of the micellar area with [cis-diaquo(trans-L-1,2-cyclohexanediamine)platinum(II) nitrate+cis-dichloro(trans-L-1,2-cyclohexanediamine)platinum(II)]/[Glu] is shown in FIG. 9. The micellar area reached the maximum at the [cis-diaquo(trans-L-1,2-cyclohexanediamine)platinum(II) nitrate+cis-dichloro(trans-L-1,2-cyclohexanediamine)platinum(II)]/[Glu] ratio of 1:1.

Example 6

This example describes a specific example in which a coexisting state of two kinds of platinum complexes is brought about in situ.

Figure 10:
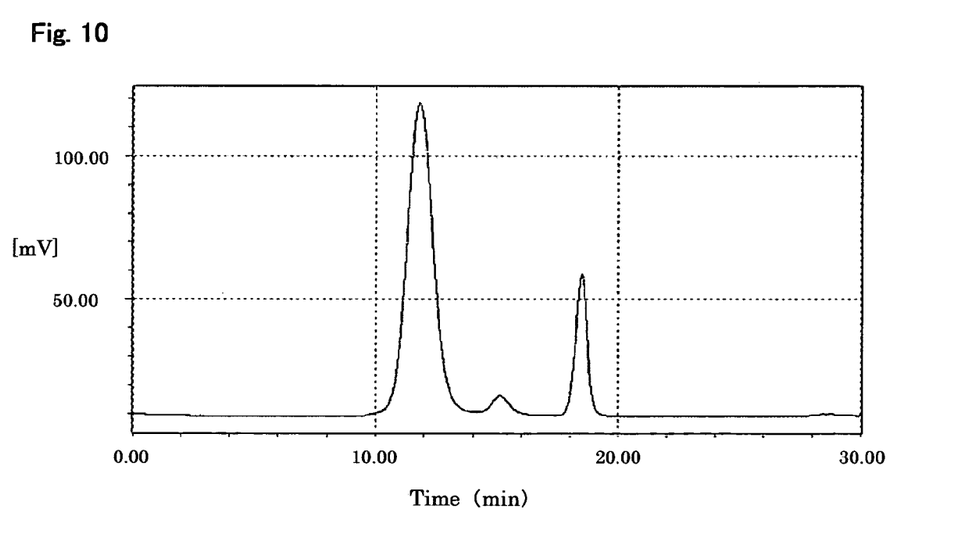
FIG. 10 is a GPC chart of the reaction solution obtained in Example 6 when the two platinum complexes were formed in situ. The abscissa axis and the ordinate axis have the same meanings as in FIG. 1.

Cis-diaquo(trans-L-1,2-cyclohexanediamine)platinum(II) nitrate was dissolved in 10 mL of water at 70° C. This solution was cooled to about 37° C., 10 μL of 1N hydrochloric acid was added thereto, 44 mg of PEG-P(Glu) 12-40 was dissolved therein {[cis-diaquo(trans-L-1,2-cyclohexanediamine)platinum(II) nitrate]/[Glu]=0.5/1}, and the resulting solution was allowed to react at 37° C. for 24 hours. A portion of the reaction solution was taken and subjected to GPC analysis under the same conditions as in Example 1. The GPC chart is shown in FIG. 10. The polymer micellar area was 8085 (mV/sec).

Example 7

This example used Dach-Pt(nitrato) alone as the starting material, to investigate the effect of its concentration in the reaction solution for forming the coordination compound, and investigated the effect of the use ratio of platinum atoms in the platinum complex to the carboxylate (Glu) in the block copolymer on the configuration of the polymer micelles formed of the coordination compounds.

Figure 11:
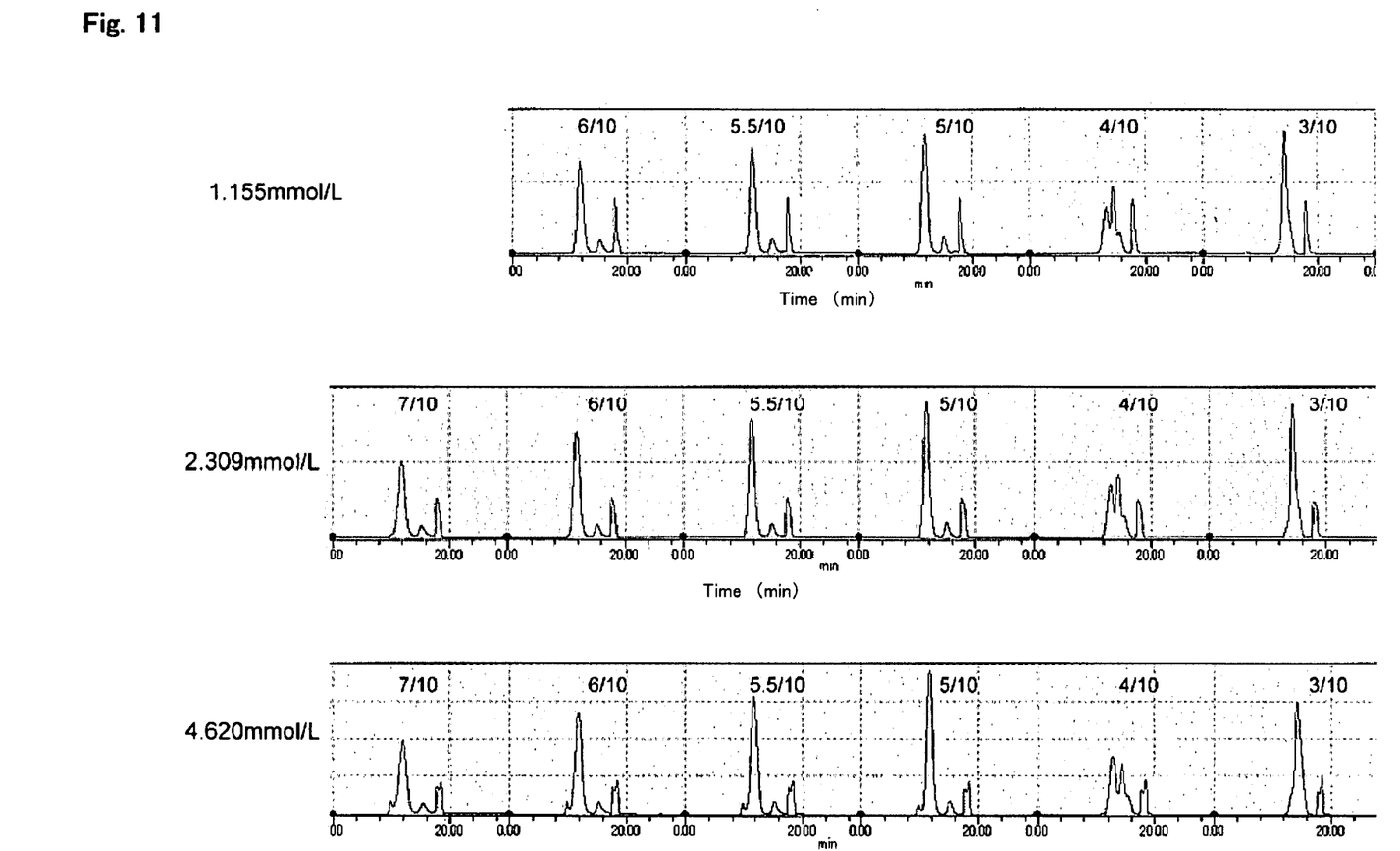
FIG. 11 shows GPC charts of the reaction solutions as obtained with varied concentration of cis-diaquo(trans-L-1,2-cyclohexanediamine)platinum(II) nitrate in the reaction solution, at varied ratio of platinum atom in cis-diaquo(trans-L-1,2-cyclohexanediamine)platinum(II) nitrate to the carboxylate in the block copolymer. The abscissa axis and the ordinate axis have the same meanings as in FIG. 1.

Cis-diaquo(trans-L-1,2-cyclohexanediamine)platinum(II) nitrate was dissolved at concentration of 4.620 mmol/L, 2.309 mmol/L and 1.155 mmol/L at 70° C., and the solutions were cooled to about 37° C. In 30 mL each of the cooled solutions with different concentration, PEG-P(Glu) 12-40 was dissolved {[cis-diaquo(trans-L-1,2-cyclohexanediamine)platinum(II) nitrate]/[Glu]=7/10, 6/10, 5.5/10, 5/10, 4/10 and 3/10}, and the resulting solutions were allowed to react at 37° C. for 72 hours in a dark place. A portion of each of the reaction solutions was taken and subjected to GPC analysis under the same conditions as in Example 1. The GPC charts obtained are shown in FIG. 11.

Although peaks of polymer micelles were detected at the positions of about 12 minutes, no peak of polymer micelle was confirmed in the reaction solutions of cis-diaquo(trans-L-1,2-cyclohexanediamine)platinum(II) nitrate at all the concentration levels, when the ratio of platinum atoms in the platinum complex to the carboxylate was 4/10 or less.

In the reaction solution having cis-diaquo(trans-L-1,2-cyclohexanediamine)platinum(II) nitrate concentration of 4.620 mmol/L, shoulder peaks were observed on the high molecular weight side of the polymer micelle peaks when the ratio of the platinum atoms in the platinum complex to the carboxylate was 7/10 to 5/10, leading to an inference that aggregated or polydispersed polymer micelles were formed.

Similarly, in the 2.309 mmol/L cis-diaquo(trans-L-1,2-cyclohexanediamine)platinum(II) nitrate reaction solution, a very small shoulder peak was observed on the high molecular weight side when the ratio of the platinum complex to the carboxylate was 7/10, but the shoulder peak disappeared and the monodispersed polymer micelles were formed at the ratios of 6/10 or less.

Also, in the 1.155 mmol/L cis-diaquo(trans-L-1,2-cyclohexanediamine)platinum(II) nitrate reaction solution, monodispersed polymer micelles were formed irrelevantly to the ratio of platinum complex to carboxylate.

From the foregoing, it is understood that monodispersed polymer micelles are more easily obtained at the concentration of cis-diaquo(trans-L-1,2-cyclohexanediamine)platinum(II) nitrate not higher than 4.620 mmol/L.

The invention claimed is:

1. A method for producing a coordination compound through reaction of a platinum complex with a polymer having carboxyl groups on its side chains, wherein a diaquoplatinum complex or a bis(nitrato)platinum complex and a dihaloplatinum complex which is selected from dichloro-, diiodo- or dibromo-platinum complexes are used in mixed state as the platinum complex, wherein the mixed state is formed by adding a halide ion selected from the group consisting of chloride, iodide and bromide ions to an aqueous solution of bis(nitrato)platinum complex or by adding a halide ion selected from the group consisting of chloride, iodide and bromide ions to aqueous solution of bis(nitrato)(1,2-cyclohexanediamine)platinum(II), and a block copolymer represented by the following general formula (1) or (2):

wherein $R^1$ represents hydrogen atom or an unsubstituted or substituted linear or branched $C_1$-$C_{12}$ alkyl group, $L^1$ and $L^2$ represent, independently of each other, linking groups, $R^2$ represents methylene group or ethylene group, $R^3$ represents hydrogen atom, a protecting group of amino group, hydrophobic group or polymerizable group, $R^4$ represents hydroxyl group, protected carboxyl group as formed together with the terminal —CO, or a hydrophobic group, $R^5$s each independently represent a hydrogen atom, alkali metal ion or a protecting group of carboxyl group, m represents an integer of 5 to 20,000, n represents an integer of 2 to 5,000, and x represents an integer of 0 to 5,000, with the proviso that x is not larger than n, and hydrogen atom or alkali metal ion occupies 50% or more of n−x and x $R^5$ s, is used as the polymer, the method comprising a step of carrying out the reaction in an aqueous medium under the conditions in which the platinum complexes and the block copolymer mutually form a coordination compound, and a step of recovering the so formed coordination compound from the reaction mixture.

2. The method according to claim 1, wherein the diaquo-platinum complex is diaquo(1,2-cyclohexanediamine)platinum(II), the bis(nitrato)platinum complex is bis(nitrato)(1,2-cyclohexanediamine)platinum(II) and the dihalo-platinum complex is selected from dichloro(1,2-cyclohexanediamine)platinum(II), diiodo(1,2-cyclohexanediamine)platinum(II) and dibromo(1,2-cyclohexanediamine)platinum(II).

3. The method according to claim 1, wherein the mixed state is formed by mixing bis(nitrato)platinum complex with dihalo-platinum complex selected from dichloro-, diiodo- and dibromoplatinum complexes.

4. The method according to claim 1, wherein the mixed state is formed by mixing bis(nitrato)(1,2-cyclohexanediamine)platinum(II) and dihalo-platinum complex selected form the group consisting of dichloro(1,2-cyclohexanediamine)platinum(II), diiodo(1,2-cyclohexanediamine)platinum(II) and dibromo(1,2-cyclohexanediamine)platinum(II).

5. The method according to claim 1, wherein the mixed state is formed by mixing dichloro(1,2-cyclohexanediamine)platinum(II) into an aqueous solution of bis(nitrato)(1,2-cyclohexanediamine)platinum(II).

6. The method according to claim 1, wherein bis(nitrato)(1,2-cyclohexanediamine)platinum(II) as bis(nitrato)platinum complex and dichloro(1,2-cyclohexanediamine)platinum(II) as dihalo-platinum complex exist at a molar ratio of 1:9 to 9:1.

7. The method according to claim 1, wherein bis(nitrato)(1,2-cyclohexanediamine)platinum(II) as bis(nitrato)platinum complex and dichloro(1,2-cyclohexanediamine)platinum(II) as dihalo-platinum complex exist at a molar ratio of 1:4 to 4:1.

8. The method according to claim 1, wherein bis(nitrato)(1,2-cyclohexanediamine)platinum(II) as bis(nitrato)platinum complex and dichloro(1,2-cyclohexanediamine)-platinum(II) as dihalo-platinum complex exist at a molar ratio of 1:1.

9. The method according to claim 1, wherein the two reactants are used in such quantities that the ratio of platinum atoms in the total platinum complexes to carboxylate groups in the block copolymer becomes 4:10 to 4:1.

10. The method according to claim 1, wherein the two reactants are used in such quantities that the ratio of platinum atoms in the total platinum complexes to carboxylate groups in the block copolymer becomes 4.5:10 to 2:1.

11. The method according to claim 1, wherein the two reactants are used in such quantities that the ratio of platinum atoms in the total platinum complexes to carboxylate groups in the block copolymer becomes 5:10 to 3:2.

12. A method for producing a coordination compound through reaction of a platinum complex and a polymer having carboxyl groups on its side chains, wherein bis(nitrato)(1,2-cyclohexanediamine)platinum(II), diaquo(1,2-cyclohexanediamine)platinum(II) or a mixture of the bis(nitrato)(1,2-cyclohexanediamine)platinum(II) and the diaquo(1,2-cyclohexanediamine)platinum (II), all of which are substantially free of silver ion, is used as starting material for the platinum complex, and a block copolymer represented by the following general formula (1) or (2):

wherein $R^1$ represents hydrogen atom or an unsubstituted or substituted linear or branched $C_1$-$C_{12}$ alkyl group, $L^1$ and $L^2$ represent, independently of each other, linking groups, $R^2$ represents methylene group or ethylene group, $R^3$ represents hydrogen atom, a protecting group of amino group, hydrophobic group or polymerizable group, $R^3$ represents hydroxyl group, protected carboxyl group as formed together with the terminal —CO, or a hydrophobic group, $R^5$s each independently represent a hydrogen atom, alkali metal ion or a protecting group of carboxyl group, m represents an integer of 5 to 20,000, n represents an integer of 2 to 5,000, and x represents an integer of 0 to 5,000, with the proviso that x is not larger than n, and hydrogen atom or alkali metal ion occupies 50% or more of n−x and x $R^5$s, is used as the polymer, the method comprising a step of carrying out the reaction in an aqueous medium under the conditions in which the platinum complex and the block copolymer mutually form a coordination compound, and a step of recovering the so formed coordination compound from the reaction mixture, wherein the ratio of platinum atoms in the platinum complex to carboxylate groups in the block copolymer in the reaction is set to be 0.475 or more to 0.6 or less.

13. The method according to claim 12, wherein the platinum complex is bis(nitrato)(1,2-cyclohexanediamine)platinum(II).

14. The method according to claim 12, wherein the ratio of platinum atoms in the platinum complex to the carboxylate groups in the block copolymer in the reaction is set to be 0.5 or more to 0.55 or less.

15. The method according to claim 12, wherein the platinum complex concentration in the aqueous medium in the reaction is set to be about 2.3 mM or less.

* * * * *

UNITED STATES PATENT AND TRADEMARK OFFICE
CERTIFICATE OF CORRECTION

PATENT NO.       : 7,781,607 B2                                   Page 1 of 1
APPLICATION NO.  : 11/921784
DATED            : August 24, 2010
INVENTOR(S)      : Katsutoshi Kobayashi It is certified that error appears in the above-identified patent and that said Letters Patent is hereby corrected as shown below:

In column 14, line 56,

"...group, $R^3$ represents hydroxyl group, protected carboxyl..."

should read

--...group, $R^4$ represents hydroxyl group, protected carboxyl...--.

Signed and Sealed this
Twenty-sixth Day of February, 2013

Teresa Stanek Rea
*Acting Director of the United States Patent and Trademark Office*